United States Patent
Park et al.

(10) Patent No.: US 9,090,522 B2
(45) Date of Patent: Jul. 28, 2015

(54) METHOD AND APPARATUS FOR RECOVERING ETHYLENE FROM FLUIDIZED CATALYTIC CRACKING (FCC) OFF-GAS

(75) Inventors: Jong Ho Park, Daejeon (KR); Jong Nam Kim, Daejeon (KR); Hee Tae Beum, Daejeon (KR); Seong Jun Lee, Daejeon (KR); Jang Jae Lee, Seongnam-si (KR); Dong Wook Kim, Daejeon (KR); Chang Hyun Ko, Daejeon (KR); Sang Sup Han, Daejeon (KR); Soon Haeng Cho, Daejeon (KR)

(73) Assignees: KOREA INSTITUTE OF ENERGY RESEARCH, Daejeon (KR); SK INNOVATION CO., LTD., Seoul (KR)

( * ) Notice: Subject to any disclaimer, the term of this patent is extended or adjusted under 35 U.S.C. 154(b) by 293 days.

(21) Appl. No.: 13/819,021

(22) PCT Filed: Aug. 26, 2011

(86) PCT No.: PCT/KR2011/006338
§ 371 (c)(1),
(2), (4) Date: Apr. 15, 2013

(87) PCT Pub. No.: WO2012/026789
PCT Pub. Date: Mar. 1, 2012

(65) Prior Publication Data
US 2014/0148634 A1 May 29, 2014

(30) Foreign Application Priority Data
Aug. 26, 2010 (KR) .................. 10-2010-0082772

(51) Int. Cl.
*C07C 7/12* (2006.01)
*B01D 53/047* (2006.01)
(Continued)

(52) U.S. Cl.
CPC ............. *C07C 7/12* (2013.01); *B01D 53/047* (2013.01); *C07C 7/13* (2013.01); *C10G 70/046* (2013.01);
(Continued)

(58) Field of Classification Search
None
See application file for complete search history.

(56) References Cited

U.S. PATENT DOCUMENTS

| 4,693,730 A | 9/1987 | Miller et al. |
| 5,906,675 A | 5/1999 | Jain et al. |

(Continued)

FOREIGN PATENT DOCUMENTS

| CN | 10-73422 A | 6/1993 |
| CN | 10-1113365 A | 1/2008 |

(Continued)

OTHER PUBLICATIONS

European Search Report for European Application No. 11820216.7 which corresponds to the above-identified U.S. application.
(Continued)

*Primary Examiner* — Tam M Nguyen
(74) *Attorney, Agent, or Firm* — LRK Patent Law Firm

(57) ABSTRACT

A method and apparatus for concentrating and recovering ethylene from the off-gas from an apparatus which produces gasoline, propylene and the like by fluidized catalytic cracking (FCC) of heavy oils such as atmospheric residue, generated in a crude oil refining process, is provided. The method and apparatus can reduce the amount of ethylene rinse in the subsequent ethylene displacement desorption process by increasing the ethylene purity of a raw material gas and reducing the concentration of weakly adsorbing components in the raw material gas and can reduce the loss of a desorbent during a distillation process for separating the desorbent from the weakly adsorbing components. Thus, ethylene can be recovered from the off-gas from fluidized catalytic cracking of heavy oils at high concentration and low cost.

25 Claims, 2 Drawing Sheets

(51) Int. Cl.
*C07C 7/13* (2006.01)
*C10G 70/04* (2006.01)

(52) U.S. Cl.
CPC ....... *B01D 2253/108* (2013.01); *B01D 2256/24* (2013.01); *B01D 2257/7022* (2013.01); *B01D 2259/4063* (2013.01); *B01D 2259/40073* (2013.01); *C10G 2300/107* (2013.01); *C10G 2300/4081* (2013.01); *C10G 2400/20* (2013.01); *Y02C 20/20* (2013.01)

(56) References Cited

U.S. PATENT DOCUMENTS

| | | | |
|---|---|---|---|
| 6,124,517 A * | 9/2000 | Kaminsky et al. | 585/829 |
| 6,293,999 B1 | 9/2001 | Cheng et al. | |
| 6,488,741 B2 | 12/2002 | Olson | |
| 6,867,166 B2 | 3/2005 | Yang et al. | |
| 2002/0007101 A1 | 1/2002 | Senetar et al. | |
| 2005/0203327 A1 | 9/2005 | Jovanovic et al. | |

FOREIGN PATENT DOCUMENTS

| | | |
|---|---|---|
| CN | 10-1652339 A | 2/2010 |
| EP | 572239 A1 | 12/1993 |
| JP | 61-126036 A | 6/1986 |
| JP | 63-88015 A | 4/1988 |
| JP | 07-207280 A | 8/1995 |
| JP | 07-251446 A | 10/1995 |
| JP | 10-053774 A | 2/1998 |
| JP | 2000-026319 A | 1/2000 |
| JP | 2002-035541 A | 2/2002 |
| JP | 2002-509083 A | 3/2002 |
| JP | 2010-532316 A | 10/2010 |
| KR | 10-0822847 B1 | 4/2008 |
| KR | 10-0849987 B1 | 7/2008 |
| KR | 10-0849987 B1 | 8/2008 |
| WO | 2008/120921 A1 | 10/2008 |

OTHER PUBLICATIONS

International Search Report for PCT Application No. PCT/KR2011/006338 filed Aug. 26, 2011.
JPO Office Action for Japanese Patent Application No. 2013-525839 which corresponds to the above-identified U.S. application.
SIPO Office Action for Chinese Patent Application No. 201180041400.1 which corresponds to the above-identified U.S. application.

* cited by examiner

METHOD AND APPARATUS FOR RECOVERING ETHYLENE FROM FLUIDIZED CATALYTIC CRACKING (FCC) OFF-GAS

TECHNICAL FIELD

The present invention relates to a method and apparatus for ethylene in concentration from the off-gas from an apparatus which produces gasoline, propylene and the like by fluidized catalytic cracking (FCC) of heavy oils such as atmospheric residue, generated in a crude oil refining process.

BACKGROUND ART

In a process of refining crude oil in an atmospheric distillation unit, low-grade heavy oils such as Bunker-C oil are produced in large amounts. When such heavy oils are introduced and treated in a fluidized catalytic cracking (FCC) unit, high-value-added light oil products such as gasoline and propylene are produced together with heavy oil and off-gas. The off-gas generated in the FCC unit is composed of hydrogen, methane, nitrogen, carbon monoxide, carbon dioxide, ethane, ethylene, propane, propylene, C4+, water and trace amounts of impurities (acidic gas, COS, H2S, arsenic, ammonia, nitrile, mercury, etc.). Although the FCC off-gas contains a large amount of ethylene as shown in Table 1 below, the concentration of ethylene in the FCC off-gas is low and the FCC off-gas contains various gases. For this reason, ethylene has not yet been recovered from the FCC off-gas in an economic manner, and the FCC off-gas has been used as fuel gas.

TABLE 1

| Components | Hydrogen (H2) | Methane (CH4) | Ethane (C2H6) | Propane (C3H8) | Ethylene (C2H4) | Propylene (C3H6) |
|---|---|---|---|---|---|---|
| Concentration (vol %) | 30.3 | 25.6 | 11.9 | 0.5 | 11.9 | 1.55 |
| Concentration (wt %) | 6.70 | 22.6 | 19.7 | 1.22 | 18.4 | 3.60 |
| Components | C4+ | Carbon monoxide (CO) | Carbon dioxide (CO2) | Nitrogen (N2) | Impurities (H2S, ammonia, etc.) | Water |
| Concentration (vol %) | 1.55 | 1.2 | 0.2 | 15.3 | Trace amounts | aturated |
| Concentration (wt %) | 1.66 | 1.86 | 0.49 | 23.7 | | |

<Composition of FCC Off-Gas (Concentration: Dry Base)>

Conventional techniques for separating light olefins (ethylene, propylene, butylene, etc.) and paraffins (ethane, propane, butane, etc.) by adsorption are as follows.

U.S. Pat. No. 6,867,166 discloses a technique of separating olefins by a pressure swing adsorption or temperature swing adsorption process using a transition metal ion-supported adsorbent having selectivity for ethylene or propylene.

Also, U.S. Pat. No. 6,293,999 discloses a technique of separating propylene from a propane/propylene mixed gas by a pressure swing or temperature swing process using an ALPO-14 adsorbent having a molecular sieve function which selectively adsorbs only propylene. Moreover, U.S. Pat. No. 6,488,741 discloses a technique of separating C2-C4 olefins by a pressure swing adsorption process or a combination of a pressure swing adsorption process with a distillation process using a zeolite adsorbent. In addition, U.S. Pat. No. 6,488,741 discloses a technique of separating propylene from a propane/propylene mixed gas using an 8-member ring adsorbent having a molecular sieve function, such as SAPO.

As described above, the processes for separating ethylene or propylene by adsorption are carried out by gas-phase adsorption rather than liquid-phase adsorption, because ethylene or propylene is not easy to liquefy. Also, the regeneration of adsorbents is performed by pressure swing adsorption or temperature swing adsorption.

Elevating and lowering the temperature of an adsorption column in the temperature swing adsorption process requires a lot of time, so that the productivity of the bulk gas separation process is low, and thus the equipment cost is high. The pressure swing adsorption or vacuum swing adsorption process is not suitable for separating large amounts of mixed gases, because the capacity of a compressor or a vacuum pump is limited.

Korean Patent Registration No. 0849987 registered in the name of the applicant discloses an adsorption separation process capable of separating ethylene from an FCC off-gas containing a low concentration of ethylene using an ethylene-selective adsorbent. The disclosed process is a displacement desorption process of desorbing adsorbed ethylene using a desorbent and is a technique of concentrating and recovering ethylene from the FCC off-gas through the sequential steps of adsorption, ethylene rinse and displacement desorption.

The concentration of ethylene in FCC off-gas is as low as about 10-20 wt %, even though it varies depending on the operating conditions of processes. In order to produce high-concentration ethylene from such FCC off-gas containing a low concentration of ethylene, rinse with a large amount of high-purity ethylene should be carried out, so that the consumption of energy in a distillation process for separating an ethylene/desorbent stream into components is disadvantageously increased, thus increasing the energy consumption of the overall process.

If the purity of ethylene is low, a paraffin/desorbent stream containing large amounts of weakly adsorbing components (hydrogen, nitrogen, methane, etc.) is discharged, and a large amount of energy is consumed to recover the desorbent in the state in which the concentration of the weakly adsorbing components is high.

The present applicants have conducted extensive studies into a technique for recovering ethylene from FCC off-gas with high purity and low cost in order to solve the above-described problems and have found that, when ethylene in the FCC off-gas is partially concentrated by a pressure swing adsorption process and high-purity ethylene is produced from a mixed gas containing the partially concentrated ethylene, ethylene can be economically recovered with high purity, thereby completing the present invention.

DISCLOSURE OF INVENTION

Technical Problem

It is an object of the present invention to provide a method and apparatus for recovering ethylene from the off-gas from fluidized catalytic cracking (FCC) of heavy oils such as atmospheric residue, generated in a crude oil refining process, with high purity and low cost.

Solution to Problem

To achieve the above object, the present invention provides a method for recovering ethylene from off-gas of a process for fluidized catalytic cracking (FCC) of a heavy oil fraction, the method comprising the processes of: concentrating the C2+ components of the FCC off-gas using a pressure swing adsorption process to obtain a C2+ rich mixed gas; and introducing the C2+ rich mixed gas into a displacement desorption process to recover high-concentration ethylene from the mixed gas.

The process of concentrating the C2+ components of the FCC off-gas by the pressure swing adsorption process comprises the steps of: i) adsorption step: introducing the FCC off-gas into an adsorption column packed with an adsorbent selectively adsorbing the C2+ components, so that the C2+ components are adsorbed onto the adsorbent and the remaining impurities are discharged out of the adsorption column; ii) rinse step: rinsing impurities away from the adsorption column with a C2 rich stream pressurized by a compressor so that the inside of the adsorption column becomes a C2+ rich atmosphere; iii) cocurrent depressurization step: discharging impurities from the adsorption column that was subjected to step ii), by cocurrent depressurization; iv) countercurrent depressurization step: countercurrently depressurizing the adsorption column that was subjected to step iii), while obtaining a partially concentrated C2 component; v) low pressure rinse step: recycling a portion of a gas discharged from the adsorption step into the adsorption column that was subjected to step iv), thereby desorbing C2+ components from the adsorption column by low-pressurerinse; and vi) pressurization step: recycling a portion of a gas discharged from the adsorption step into the adsorption column that was subjected to step iv), and pressurizing the adsorption column to the adsorption pressure; wherein each of steps i) to vi) may be periodically repeated in a manner and different steps may be carried out in a plurality of adsorption columns.

The process of introducing the C2+ rich mixed gas into the displacement desorption process to recover high-concentration ethylene comprises: i) recovery step: recovering gases discharged from adsorption and ethylene rinse into an adsorption column packed with an ethylene selective adsorbent, thereby obtaining a C2+ rich mixed gas; ii) adsorption step: introducing the C2+ rich mixed gas into the ethylene selective adsorbent-packed adsorption column to adsorb ethylene from the mixed gas, and introducing unadsorbed components and a desorbent, fed into the adsorption column during desorption, through the outlet of the adsorption column into a distillation column that separates an ethylene-poor stream/desorbent mixture into components; iii) ethylene rinse step: introducing a high-concentration ethylene, obtained in a distillation column for separating an ethylene rich stream/desorbent mixture into components, into the adsorption column that was subjected to step ii), thereby removing ethane and other gases; and iv) desorption step: introducing a desorbent into the adsorption column that was subjected to step iii) so as to desorb ethylene from the adsorption column, and then sending the desorbed ethylene into the distillation column for separating the ethylene rich stream/desorbent mixture into components, thereby producing concentrated ethylene; wherein the steps i) to iv) may be repeatedly carried out in a plurality of adsorption column, and each of adsorption columns may be performed the different steps.

The present invention also provides an apparatus for recovering ethylene from fluidized catalytic cracking (FCC) off-gas, which comprises: a pressure swing adsorption unit for concentrating C2+ components from an off-gas from a process for fluidized catalytic cracking (FCC) of a heavy oil fraction to obtain a C2+ rich mixed gas; and an ethylene displacement desorption unit for selectively separating ethylene from the C2+ rich mixed gas.

BRIEF DESCRIPTION OF DRAWINGS

The above and other objects, features and advantages of the present invention will be more clearly understood from the following detailed description taken in conjunction with the accompanying drawing, in which.

MODE FOR THE INVENTION

Hereinafter, the present invention will be described in detail with reference to the accompanying drawings.

Figure 1:
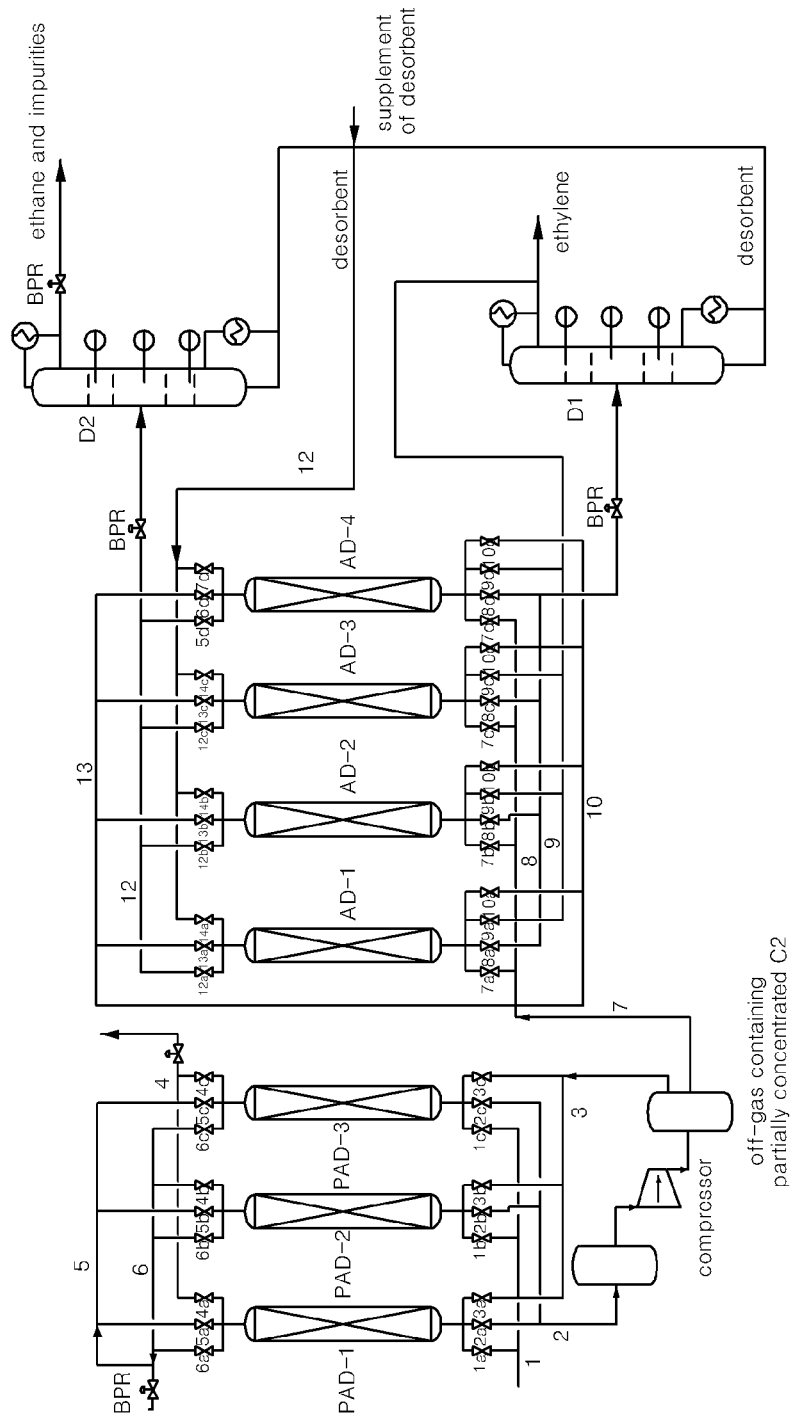
FIG. 1 is a schematic view of an apparatus for recovering ethylene from fluidized catalytic cracking (FCC) off-gas according to the present invention.

FIG. 1 is a schematic view of an apparatus for recovering ethylene from fluidized catalytic cracking (FCC) off-gas according to the present invention.

The present invention provides a method for recovering ethylene from off-gas of a process for fluidized catalytic cracking (FCC) of a heavy oil fraction, the method comprising the processes of: concentrating the C2+ components of the FCC off-gas using a pressure swing adsorption process to obtain a C2+ rich mixed gas; and introducing the C2+ rich mixed gas into a displacement desorption process to recover high-concentration ethylene from the mixed gas.

The method for recovering ethylene from fluidized catalytic cracking (FCC) off-gas according to the present invention comprises: a pressure swing adsorption process (PSA process) for partially concentrating C2+ components from the FCC off-gas; and a displacement desorption process for recovering ethylene from a stream containing the partially concentrated C2+ components.

In the method for recovering ethylene from fluidized catalytic cracking (FCC) off-gas according to the present invention, in order to recover high-purity ethylene at low cost, the process of concentrating the C2+ components of the FCC off-gas using the pressure swing adsorption process is carried out, after which the process of introducing the C2+ rich stream into an ethylene displacement desorption process to recover high-concentration ethylene is carried out.

The process of concentrating the C2+ components of the FCC off-gas by the pressure swing adsorption process comprises the steps of: i) adsorption step: introducing the FCC off-gas into an adsorption column packed with an adsorbent selectively adsorbing the C2+ components, so that the C2+ components are adsorbed onto the adsorbent and the remaining impurities are discharged out of the adsorption column; ii)

rinse step: rinsing impurities away from the adsorption column with a C2 rich stream pressurized by a compressor so that the inside of the adsorption column becomes a C2+ rich atmosphere; iii) concurrent depressurization step: discharging impurities from the adsorption column that was subjected to step ii), by cocurrent depressurization; iv) countercurrent depressurization step: countercurrently depressurizing the adsorption column that was subjected to step iii), while obtaining a partially concentrated C2 component; v) low pressure rinse step: recycling a portion of a gas discharged from the adsorption step into the adsorption column that was subjected to step iv), thereby desorbing C2+ components from the adsorption column by low-pressure rinse; and vi) pressurization step: recycling a portion of a gas discharged from the adsorption step into the adsorption column that was subjected to step v), and pressurizing the adsorption column to the adsorption pressure; wherein each of steps i) to vi) may be periodically repeated in a plurality of adsorption columns. Also, each of adsorption columns may be repeatedly performed the different configurations in a plurality of adsorption columns.

In one embodiment of the present invention, the process of concentrating the C2+ components of the FCC off-gas using the pressure swing adsorption process may be carried out in two or three adsorption columns as shown in Tables 2 and 3. In one embodiment of the present invention, the pressure swing adsorption process may be carried out in at least two adsorption columns.

In this case, the pressure equalization step may be carried out through concurrent depressurization step: discharging impurities from the adsorption column that was subjected to adsorption step, by cocurrent depressurization and partial pressurization step: recycling a portion of a gas discharged from the adsorption step into the adsorption column that was subjected to low pressure rinse step, and pressurizing the adsorption column.

In other words, the adsorption, concurrent depressurization, countercurrent depressurization, low-pressure rinse, partial pressurization and pressurization steps in the process of concentrating the C2+ components of the FCC off-gas using the pressure swing adsorption process may be repeatedly carried out in each of adsorption columns.

Referring to Table 3 above, in another embodiment of the present invention, the adsorption, rinse, cocurrent depressurization, countercurrent depressurization, low-pressure rinse and pressurization steps in the process of concentrating the C2+ components of the FCC off-gas using the pressure swing adsorption process may be carried out the different steps with each other in three adsorption columns (PAD-1, PAD-2 and PAD-3) so that the C2+ components in the FCC off-gas can be highly concentrated.

The adsorption and rinse steps in the process of concentrating the C2+ components of the FCC off-gas using the pressure swing adsorption process are preferably carried out under conditions of a pressure of 2~10 atm and a temperature

TABLE 2

|  | t1 | t2 | t3 | t1 | a | t3 |
|---|---|---|---|---|---|---|
| PAD-1 | Adsorption | Pressure equalization | Countercurrent depressurization | Low-pressure rinse | Pressure equalization | Pressurization |
| PAD-2 | Low-pressure rinse | Pressure equalization | Pressurization | Adsorption | Pressure equalization | Countercurrent depressurization |

TABLE 3

|  | t1 | t2 | t3 | t1 | t2 | t3 | t1 | t2 | t3 |
|---|---|---|---|---|---|---|---|---|---|
| PAD-1 | Adsorption | | | Rinse | Cocurrent depressurization | Countercurrent depressurization | Low-pressure rinse | Pressurization | |
| PAD-2 | Low-pressure rinse | Pressurization | | Adsorption | | | Rinse | Cocurrent depressurization | Countercurrent depressurization |
| PAD-3 | Rinse | Cocurrent depressurization | Countercurrent depressurization | Low-pressure rinse | Pressurization | | Adsorption | | |

Referring to Table 2 above, in one embodiment of the present invention, the adsorption, pressure equalization, countercurrent depressurization, low-pressure rinse and pressurization steps in the process of concentrating the C2+ components of the FCC off-gas using the pressure swing adsorption process may be carried out the different configurations with each other in two adsorption columns (PAD-1 and PAD-2) so that the C2+ components in the FCC off-gas can be highly concentrated.

of 20~150° C., and the low-pressure rinse and countercurrent depressurization steps are preferably carried out at a pressure of 1-4 atm.

The C2 concentrated stream obtained in the low-pressure rinse and countercurrent depressurization steps is introduced into an ethylene displacement desorption process through a compressor, in which the stream is preferably compressed to a pressure of 3-20 atm through the compressor.

The adsorbent that selectively adsorbs the C2+ components may be silica gel, zeolite, activated carbon or the like.

The process of introducing the C2+ rich mixed gas into the ethylene displacement desorption process to recover a high concentration of ethylene comprises the steps of: i) recovery step: recovering gas (a mixed gas of weakly adsorbing components such as ethane, nitrogen, methane, carbon monoxide, hydrogen or the like and a desorbent) discharged from adsorption and ethylene rinse into an adsorption column packed with an ethylene selective adsorbent, thereby obtaining a C2+ rich mixed gas; ii) adsorption step: introducing the C2+ rich mixed gas into the ethylene selective adsorbent-packed adsorption column to adsorb ethylene from the mixed gas, and introducing unadsorbed components and a desorbent, fed into the adsorption column during desorption step, through the outlet of the adsorption column into a distillation column that separates an ethylene-poor stream/desorbent mixture into components; iii) ethylene rinse step: introducing a high-concentration ethylene, obtained in a distillation column for separating an ethylene rich stream/desorbent mixture into components, into the adsorption column that was subjected to step ii), thereby removing ethane and other gases; and iv) desorption step: introducing a desorbent into the adsorption column that was subjected to step iii) so as to desorb ethylene from the adsorption column, and then sending the desorbed ethylene into the distillation column for separating the ethylene rich stream/desorbent mixture into components, thereby producing concentrated ethylene; wherein the steps i) to iv) may be repeatedly carried out in a plurality of adsorption columns. Also, each of adsorption columns may be repeatedly performed the different configurations.

The process of introducing the C2+ rich mixed gas into the ethylene displacement desorption process to recover high-concentration ethylene can be operated by carrying out the recovery, adsorption, ethylene rinse and desorption steps in four adsorption columns (AD-1, AD-2, AD-3 and AD-4) as shown in Tables 4 and 5 below.

TABLE 4

| Time | t1 | t1 | t1 | t1 |
| --- | --- | --- | --- | --- |
| AD-1 | Recovery | Adsorption | Ethylene rinse | Desorption |
| AD-2 | Desorption | Recovery | Adsorption | Ethylene rinse |
| AD-3 | Ethylene rinse | Desorption | Recovery | Adsorption |
| AD-4 | Adsorption | Ethylene rinse | Desorption | Recovery |

TABLE 5

| Time | t1 | t1 | t1 | t1 |
| --- | --- | --- | --- | --- |
| AD-1 | Adsorption | Recovery | Ethylene rinse | Desorption |
| AD-2 | Desorption | Adsorption | Recovery | Ethylene rinse |
| AD-3 | Ethylene rinse | Desorption | Adsorption | Recovery |
| AD-4 | Recovery | Ethylene rinse | Desorption | Adsorption |

As shown in Tables 4 and 5 above, the process of introducing the C2+ rich mixed gas into the ethylene displacement desorption process to recover high-concentration ethylene may either consist of recovery step-adsorption step-ethylene rinse-step-desorption step or consist of adsorption step-recovery step-ethylene rinse step-desorption step.

If the pressure in the ethylene adsorption step is atmospheric pressure or higher, the process may further comprise, before the ethylene rinse step, a cocurrent depressurization step of discharging the remaining components other than ethylene.

Preferably, the process of introducing the C2+ rich mixed gas into the ethylene displacement desorption process to recover a high concentration of ethylene may further comprise: a pressure equalization step of communicating the adsorption column after the adsorption step with the adsorption column after the desorption step to send components other than ethylene from the adsorption column that was subjected to the adsorption step to the adsorption column that was subjected to the desorption step, thereby depressurizing the adsorption column that was subjected to the adsorption step and pressurizing the adsorption column that was subjected to the desorption step; a cocurrent depressurization step of discharging components other than ethylene from the adsorption columns that was subjected to the pressure equalization step; and a pressurization step of introducing the C2+ rich mixed gas into the adsorption columns that were subjected to the pressure equalization step, thus pressurizing the adsorption columns to the adsorption pressure.

As the ethylene selective adsorbent, a π-complex adsorbent selectively forming a π-complex with ethylene, a zeolite X adsorbent, a zeolite Y adsorbent or a zeolite A adsorbent may be used. Preferably, a zeolite 13X adsorbent may be used.

The desorption step is preferably carried out under conditions of a pressure of 1-10 atm and a temperature of 20~150° C.

The desorbents separated from the distillation column separating the ethylene-stripped stream/desorbent mixture and from the distillation column separating the ethylene rich stream/desorbent mixture may be recycled to the adsorption column.

The desorbent that is used in the present invention may be a C3-C6 hydrocarbon, but is not limited thereto.

The present invention also provides an apparatus for recovering ethylene from fluidized catalytic cracking (FCC) off-gas, which comprises: a pressure swing adsorption unit for concentrating C2+ components from an off-gas from a process for fluidized catalytic cracking (FCC) of a heavy oil fraction to obtain a C2+ rich mixed gas; and an ethylene displacement desorption unit for selectively separating ethylene from the C2+ rich mixed gas.

The apparatus for recovering ethylene from FCC off-gas according to the present invention comprises a pressure swing adsorption unit for concentrating C2+ components from an off-gas from a process for fluidized catalytic cracking (FCC) of a heavy oil fraction, so that high-purity ethylene can be obtained. The pressure swing adsorption unit for concentrating C2+ components comprises FCC off-gas supply pipeline; a pipeline connecting a C2+ rich stream, discharged from the countercurrent depressurization and low-pressure rinse steps, with a compressor; a pipeline for supplying a portion of the desorbed gas (a C2+ rich mixed gas) compressed by the compressor to the adsorption column in order to perform the rinse step; a pipeline for discharging high concentrations of impurities from the adsorption column during the adsorption step; a pipeline for supplying high concentrations of impurities, discharged from the adsorption step, to the low-pressure rinse step for regenerating the adsorbent; a plurality of adsorption columns packed with an adsorbent selectively adsorbing C2+ components, in which the adsorption columns are connected with a pipeline for discharging gas from the cocurrent depressurization step to the outside; and a compressor for compressing a mixed gas discharged from the desorption and low-pressure rinse steps.

In one embodiment of the present invention, the pressure swing adsorption unit for concentrating the C2+ components comprises: three adsorption columns (PAD-1, PAD-2 and PAD-3), which are packed with an adsorbent selectively adsorbing the C2+ components; and a compressor for compressing the C2+ components, which are discharged during the desorption process, by the operating pressure of the subsequent ethylene displacement desorption process.

Referring to FIG. 1, the pressure swing adsorption unit for concentrating the C2+ components comprises:

an adsorption column (PAD-1) packed with an adsorbent selectively adsorbing C2+ components, in which the lower portion of the adsorption column (PAD-1) is connected with an FCC off-gas supply pipeline via a valve 1a and is connected via a valve 2a with a pipeline 2 connecting a C2+ rich stream, discharged from the countercurrent depressurization and low-pressure rinse steps, with a compressor, in which the adsorption column (PAD-1) is provided with a pipeline 3 and valve 3a for supplying a portion of the desorbed gas (a C2+ rich mixed gas) compressed by the compressor to the adsorption column in order to perform the rinse step, is connected with a pipeline 6 and valve 6a for discharging high concentrations of impurities from the adsorption column during the adsorption step, is connected with a pipeline 5 and valve 5a for supplying high concentrations of impurities, discharged from the adsorption step, to the low-pressure rinse step for regenerating the adsorbent, and is connected with a pipeline 4 and valve 4a for discharging gas from the cocurrent depressurization step to the outside;

an adsorption column (PAD-2) packed with an adsorbent selectively adsorbing C2+ components, in which the lower portion of the adsorption column (PAD-2) is connected with an FCC off-gas supply pipeline 1 via a valve 1b and is connected via a valve 2b with a pipeline 2 connecting a C2+ rich stream, discharged from the countercurrent depressurization and low-pressure rinse steps, with a compressor, in which the adsorption column (PAD-2) is provided with a pipeline 3 and valve 3b for supplying a portion of the desorbed gas (a C2+ rich mixed gas) compressed by the compressor to the adsorption column in order to perform the rinse step, is connected with a pipeline 6 and valve 6b for discharging high concentrations of impurities from the adsorption column during the adsorption step, to the outside, is connected with a pipeline 5 and valve 5b for supplying high concentrations of impurities, discharged from the adsorption step, to the low-pressure rinse step for regenerating the adsorbent, and is connected with a pipeline 4 and valve 4b for discharging gas from the cocurrent depressurization step to the outside;

an adsorption column (PAD-3) packed with am adsorbent selectively adsorbing C2+ components, in which the lower portion of the adsorption column (PAD-3) is connected with an FCC off-gas supply pipeline 1 via a valve 1c and is connected via a valve 2c with a pipeline 2 connecting a C2+ rich stream, discharged from the countercurrent depressurization and low-pressure rinse steps, with a compressor, in which the adsorption column (PAD-3) is provided with a pipeline 3 and valve 3c for supplying a portion of the desorbed gas (a C2+ rich mixed gas) compressed by the compressor to the adsorption column in order to perform the rinse step, is connected with a pipeline 6 and valve 6c for discharging high concentrations of impurities from the adsorption column during the adsorption step, to the outside, is connected with a pipeline 5 and valve 5c for supplying high concentrations of impurities, discharged from the adsorption step, to the low-pressure rinse step for regenerating the adsorbent, and is connected with a pipeline 4 and valve 4c for discharging gas from the cocurrent depressurization step to the outside; and a compressor for compressing a mixed gas discharged from the desorption and low-pressure rinse steps;

wherein the adsorption, rinse, cocurrent depressurization, countercurrent depressurization, low-pressure rinse and pressurization steps which are consecutive may be repeatedly carried out in the three adsorption columns.

Hereinafter, in one embodiment, the one-cycle operation of the pressure swing adsorption process for concentrating C2+ components from FCC off-gas will be described with reference to Table 3 above.

First, the adsorption step is carried out in which the FCC off-gas is supplied to the adsorption column (PAD-1) packed with a C2 selective adsorbent via the FCC supply pipeline 1 and the valve 1a so that the C2+ components of the gas are selectively adsorbed and weakly adsorbing impurity components are discharged to the outside via the pipeline 6 and the valve 6a.

While the adsorption step is carried out in the adsorption column (PAD-1), the low-pressure rinse step for desorbing C2+ components using a portion of the gas discharged from the adsorption column (PAD-1) is carried out in the adsorption column (PAD-2). The gas required for the low-pressure rinse step is supplied to the adsorption column (PAD-2) via the pipeline 5 and the valve 5b, and the C2+ rich gas is discharged through the pipeline 2 and the valve 2b and pressurized through the compressor to the pressure required for the subsequent ethylene displacement desorption process. When the low-pressure rinse step in the adsorption column (PAD-2) is completed, the pressurization step of pressurizing the adsorption column (PAD-2) to the adsorption pressure using the off-gas discharged from the adsorption column during the adsorption step is carried out, and gas required to pressurize the adsorption column (PAD-2) is supplied through the pipeline 6 and the valve 6b. While the adsorption step is carried out in the adsorption column (PAD-1), the adsorption column (PAD-3) performs the rinse step of removing other impurities from the adsorption column using the C2+ rich desorbed gas, the cocurrent depressurization step of removing a portion of impurities from the adsorption column after the rinse step by cocurrent depressurization, and the countercurrent step of recovering the C2+ components adsorbed onto the adsorbent.

Each of the steps is carried out in the following manner. The gas required for the rinse step for removing impurities from the adsorption column (PAD-3) is supplied through the pipeline 3 and the valve 3c by compressing the C2 rich mixed gas resulting from the countercurrent depressurization and low-pressure rinse steps with the compressor, and in this process, impurities are discharged from the top of the adsorption column through the pipeline 6 and the valve 6c. After completion of the rinse step, the adsorption column is cocurrently depressurized through the pipeline 4 and the valve 4c, and the gas generated during the cocurrent depressurization is discharged to the outside. When the adsorption column is depressurized to a given level, it is depressurized to atmospheric pressure through the pipeline 2 and the valve 2c, and the C2 rich gas obtained in this depressurization process is compressed through the compressor.

When the adsorption step in the adsorption column PAD-2 has completed, an adsorption step in which the FCC off-gas is supplied to the adsorption column PAD-3 is carried out. While the adsorption step in the adsorption column PAD-3 is carried out, the low-pressure rinse and pressurization steps of regenerating the adsorbent using a low-concentration C2-containing off-gas discharged from the adsorption step are carried out in the adsorption column PAD-1, and the rinse step of rinsing impurity components away from the adsorption column using a C2-rich gas, the cocurrent depressurization step of lowering the pressure of the adsorption column to remove impurities, and the countercurrent depressurization step for obtaining a C2 rich gas are carried out in the adsorption column PAD-3. While the above-described periodic operation is continuously repeated, the C2 component of the FCC off-gas is concentrated.

As described in Table 3 above, the process operation in which the adsorption step in the adsorption column PAD-1 is carried out while the other two columns are operated has been described. When the adsorption step in the adsorption column (PAD-1) is completed, an adsorption step in which the FCC off-gas is supplied to the adsorption column PAD-2 is carried out. While the adsorption step in the adsorption column PAD-2 is being carried out, the rinse, cocurrent depressurization and countercurrent depressurization steps are carried out in the other adsorption column PAD-1, and the low-pressure rinse and pressurization steps are carried out in the adsorption column PAD-3.

But each of adsorption columns need not be carried out different steps with each other at the same time. Preferably, each of adsorption columns may be carried out different configurations so as to improve concentration efficiency.

In one embodiment of the present invention, the ethylene displacement desorption unit for selectively separating ethylene from the C2+ rich mixed gas comprises a plurality of adsorption columns which is connected via a C2+ rich mixed gas supply pipeline with the pressure swing adsorption unit for concentrating the C2+ components, is connected with an ethylene rich stream/desorbent discharge pipeline leading to the distillation column D1, a pipeline for supplying a given amount of the ethylene rich stream from the distillation column D1, a pipeline for introducing a mixed gas discharged from the adsorption and ethylene rinse steps into the adsorption column. a pipeline for guiding the ethylene poor stream and desorbent discharged from the recovery step into the distillation column D2, and a pipeline for supplying the desorbent, separated from the distillation column D1 and the distillation column D2, to the adsorption column; and at least two distillation columns, including a distillation column (D1) for separating an olefin rich stream/desorbent mixture into components, and a distillation column (D2) for separating an olefin poor stream/desorbent into components.

Referring to FIG. 1, in one embodiment of the present invention, the ethylene displacement desorption unit for selectively separating ethylene from the C2+ rich mixed gas is a unit for selectively separating ethylene from the C2+ rich FCC off-gas and comprises four adsorption columns (AD-1, AD-2, AD-3 and AD-4) packed with an adsorbent selectively adsorbing ethylene, and two distillation columns, one of which is a distillation column D1 for separating an ethylene rich stream/desorbent mixture into components and the other of which is a distillation column D2 for separating an ethylene poor stream/desorbent mixture into components.

Referring to FIG. 1, the ethylene displacement desorption unit for selectively separating ethylene from the C2+ rich mixed gas comprises:

an ethylene selective adsorbent-packed adsorption column AD-1 which is connected via a C2+ rich mixed gas supply pipeline 7 and a valve 7a with the pressure swing adsorption unit for concentrating the C2+ components, is connected via a valve 8a with an ethylene rich stream/desorbent discharge pipeline 8 leading to the distillation column D1, is connected via a valve 9a with a pipeline 9 for supplying a given amount of the ethylene rich stream from the distillation column D1, is connected via a valve 10a with a pipeline 10 for introducing a mixed gas discharged from the adsorption and ethylene rinse steps into the adsorption column that was subjected to the desorption step, is connected via a valve 12a with a pipeline 12 for guiding the ethylene poor stream and desorbent discharged from the recovery step into the distillation column D2, and is connected via a valve 14a with a pipeline for supplying the desorbent, separated from the distillation column D1 and the distillation column D2, to the adsorption column;

an ethylene selective adsorbent-packed adsorption column AD-2 which is connected via a C2+ rich mixed gas supply pipeline 7 and a valve 7b with the pressure swing adsorption unit for concentrating the C2+ components, is connected via a valve 8b with an ethylene rich stream/desorbent discharge pipeline 8 leading to the distillation column D1, is connected via a valve 9b with a pipeline 9 for supplying a given amount of the ethylene rich stream from the distillation column D1, is connected via a valve 10b with a pipeline 10 for introducing a mixed gas discharged from the adsorption and ethylene rinse steps into the adsorption column having been subjected to the desorption step, is connected via a valve 12b with a pipeline 12 for guiding the ethylene poor stream and desorbent discharged from the recovery step into the distillation column D2, and is connected via a valve 14b with a pipeline for supplying the desorbent, separated from the distillation column D1 and the distillation column D2, to the adsorption column;

an ethylene selective adsorbent-packed adsorption column AD-3 which is connected via a C2+ rich mixed gas supply pipeline 7 and a valve 7c with the pressure swing adsorption unit for concentrating the C2+ components, is connected via a valve 8c with an ethylene rich stream/desorbent discharge pipeline 8 leading to the distillation column D1, is connected via a valve 9c with a pipeline 9 for supplying a given amount of the ethylene rich stream from the distillation column D1, is connected via a valve 10c with a pipeline 10 for introducing a mixed gas discharged from the adsorption and ethylene rinse steps into the adsorption column having been subjected to the desorption step, is connected via a valve 12c with a pipeline 12 for guiding the ethylene poor stream and desorbent discharged from the recovery step into the distillation column D2, and is connected via a valve 14c with a pipeline for supplying the desorbent, separated from the distillation column D1 and the distillation column D2, to the adsorption column;

an ethylene selective adsorbent-packed adsorption column AD-4 which is connected via a C2+ rich mixed gas supply pipeline 7 and a valve 7d with the pressure swing adsorption unit for concentrating the C2+ components, is connected via a valve 8d with an ethylene rich stream/desorbent discharge pipeline 8 leading to the distillation column D1, is connected via a valve 9d with a pipeline 9 for supplying a given amount of the ethylene rich stream from the distillation column D1, is connected via a valve 10d with a pipeline 10 for introducing a mixed gas discharged from the adsorption and ethylene rinse steps into the adsorption column having been subjected to the desorption step, is connected via a valve 12d with a pipeline 12 for guiding the ethylene poor stream and desorbent discharged from the recovery step into the distillation column D2, and is connected via a valve 14d with a pipeline 11 for supplying the desorbent, separated from the distillation column D1 and the distillation column D2, to the adsorption column; and two distillation columns, one of which is a distillation column D1 for separating an ethylene-rich stream/desorbent mixture into components and the other of which is a distillation column D2 for separating an ethylene-poor stream/desorbent mixture into components; wherein the recovery step, the adsorption step, the ethylene rinse step and the desorption step may be repeatedly carried out in the adsorption column, preferably each of four adsorption columns may be carried out the different configurations.

Hereinafter, the one-cycle operation of the ethylene displacement desorption process for selectively separating ethylene from the C2-rich mixed gas will be described with reference to Table 4 above.

First, the gases discharged from the adsorption and ethylene rinse steps are incorporated into the pipeline 13 and introduced via the valve 10a into the adsorption column AD-1 that was subjected to desorption. At this time, ethylene in the mixed gas is selectively adsorbed in the adsorption column, and weakly adsorbing components, such as hydrogen, nitrogen, carbon monoxide, methane and ethane, together with a desorbent present in the adsorption column after the desorption step, are introduced via the pipeline 12 and the valve 12a into the distillation column D2 for separating the desorbent from the weakly adsorbing components, thus recovering the desorbent.

While the adsorption column AD-1 is subjected to the recovery step, the adsorption column AD-2 is subjected to the desorption step of desorbing adsorbed ethylene using a desorbent. The desorbent used is obtained from the bottom of the distillation columns D1 and D2 and introduced into the adsorption column AD-2 through the pipeline 11 and the valve 14b. The ethylene rich stream which is discharged together with the desorbent is introduced through the valve 8b and the pipeline 8 into the distillation column D1 in which the ethylene rich stream is separated from the desorbent. Also, a portion of the ethylene rich stream separated from the distillation column D1 is introduced through the pipeline 9 and the valve 9c into the adsorption column AD-3 so that trace amounts of ethane and other gases adsorbed together with ethylene are removed, thus increasing the purity of ethylene (ethylene rinse step). At this time, the gas discharged from the adsorption column AD-3 is introduced into the adsorption column AD-1 through the valve 13c and the pipeline 13. The adsorption column AD-4 is subjected to the adsorption step of adsorbing the ethylene components of the C2+ rich mixed gas which is supplied through the pipeline 7 and the valve 7d.

As shown in Table 4 above, when the recovery step in the adsorption column AD-1 has completed, the adsorption column AD-1 is subjected to the adsorption step of selectively adsorbing ethylene components from the C2+ rich mixed gas. At the same time, the adsorption column AD-2 that was subjected to the desorption step is subjected to the recovery step of adsorbing ethylene components from the gases discharged from the adsorption column AD-1 (adsorption step) and the adsorption column AD-4 (ethylene rinse step), and the adsorption column AD-3 is subjected to the desorption step of desorbing ethylene with the desorbent, and the adsorption column AD-4 is subjected to the ethylene rinse step of removing small amounts of ethane, methane and the like from the adsorption column with the high-concentration ethylene obtained in the distillation column D1. When one adsorption column is subjected to recovery step-adsorption step-ethylene rinse step-desorption step as described above, the one-cycle operation has completed and is followed by the next cycle operation.

Also, the displacement desorption process for selectively separating ethylene from the C2+ rich mixed gas may be operated in the order of adsorption step-recovery step-ethylene rinse step-desorption step depending on the ethylene concentration of the FCC off-gas. Specifically, if the ethylene concentration of the C2+ rich mixed gas is high, the ethylene displacement desorption process may be operated in order of the adsorption step of introducing the C2+ rich mixed gas into the adsorption column that was subjected to desorption so as to selectively separate ethylene from the mixed gas, the recovery step of recovering ethylene from the off-gas discharged from the ethylene rinse step, the ethylene cleaning step of removing impurities from the adsorption column after the recovery step using high-concentration ethylene obtained from the distillation column D1, and the desorption step of introducing the desorbent into the adsorption column that was subjected to the ethylene rinse step so as to desorb ethylene from the adsorption column.

In addition, when the pressure of the adsorption step is greater than atmospheric pressure, the ethylene displacement desorption process for selectively separating ethylene from the C2+ rich mixed gas may further comprise, before the rinse step, a cocurrent depressurization step of discharging components other than ethylene from the adsorption column.

Hereinafter, preferred examples of the present invention will be described in detail.

Example 1

Figure 2:
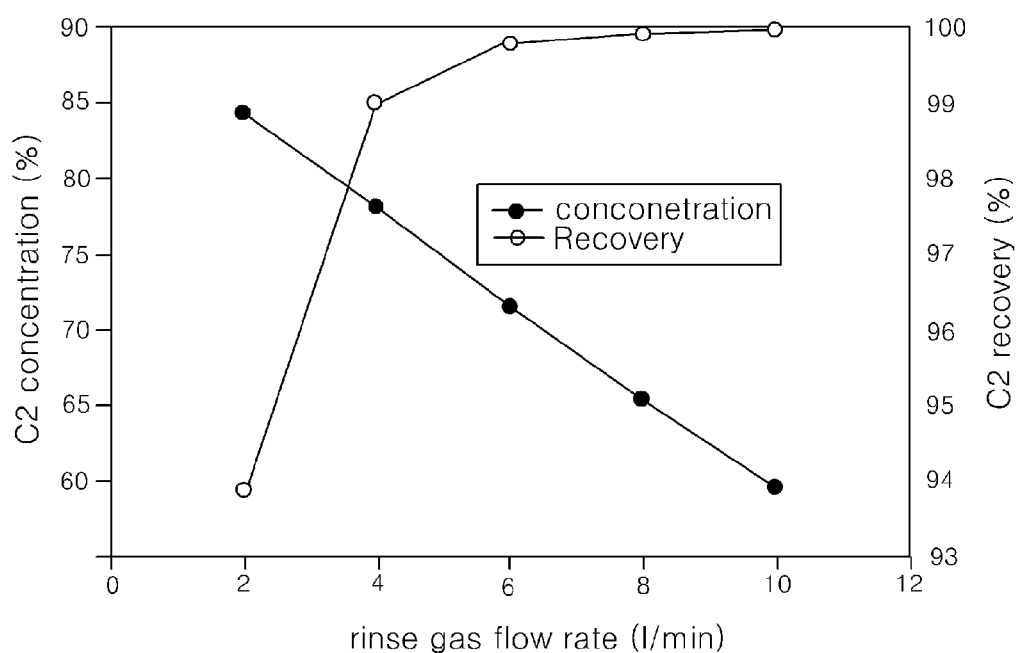
FIG. 2 is a graph showing the concentration and recovery rate of C2 in a C2 rich stream obtained by carrying out an ethylene recovery process according to the inventive method for recovering ethylene from fluidized catalytic cracking (FCC) off-gas in Example 1 of the present invention.

First, how C2+ components can be concentrated by a pressure swing adsorption (PSA) process was examined by computer simulation. Table 6 below shows the concentration of each component used in the computer simulation. The adsorption columns were packed with silica gel, the adsorption pressure was set at 10 atm, the desorption pressure was set at 1 atm, and the rinse flow rate was set at 67% of the total amount of desorbed gas. The adsorption columns were operated according to the process configuration shown in Table 3 above, and FIG. 2 shows the concentration and recovery (%) of C2 in a C2 rich stream obtained by the computer simulation. As shown in FIG. 2, concentrating the C2 component was possible, and the C2 component could be obtained at a concentration of 78% based on a recovery ratio of 99%.

TABLE 6

| Component | Concentration (vol %) |
|---|---|
| H2 | 27 |
| N2 | 10 |
| Methane | 30 |
| C2 | 32 |
| C3 | 1 |

Test Example 1

Test for Measuring the Efficiency of a Method for Recovering Ethylene Using a Pressure Swing Adsorption Process for Concentrating C2+ Components The efficiency of the method of recovering ethylene using a pressure swing adsorption process for concentrating C2+ components was examined through an experiment. For this purpose, the performance of an ethylene displacement desorption process, obtained when operating the process using raw material gases having the different ethylene compositions shown in Table 7 below, was compared between the compositions, and the results of the comparison are shown in Table 8 below.

Table 7

TABLE 7

| Component | Composition I (vol %) | Composition II (vol %) |
|---|---|---|
| H2 | 21.16 | 5.5 |
| N2 | 10.51 | 6.8 |

TABLE 7-continued

| Component | Composition I (vol %) | Composition II (vol %) |
|---|---|---|
| Methane | 34.22 | 22.2 |
| Ethane | 13.34 | 24.6 |
| Ethylene | 19.41 | 40.4 |
| Propane | 0.01 | 0.1 |
| Propylene | 1.35 | 0.4 |
| Sum | 100.00 | 100.00 |

The ethylene displacement desorption process was carried out according to the configuration shown in Table 4 above using the inventive apparatus for recovering ethylene from fluidized catalytic cracking (FCC) off-gas as shown in FIG. 1. Using 13X zeolite as an adsorbent for ethylene separation and a C4 mixed gas (95% isobutane and 5% n-butane) as a desorbent, an experiment for separating ethylene components from the mixed gases having the compositions shown in Table 7 according to the process configuration shown in Table 4 was carried out. The adsorption step was operated at 80° C. and 8 bar, and as ethylene required for high-purity ethylene rinse, commercially available high-purity ethylene (99.95%) was used without distillation.

TABLE 8

| Raw material gas | Composition I | Composition II |
|---|---|---|
| Operating conditions | | |
| Raw material flow rate (NL/hr) | 1498 | 689 |
| Rinse flow rate (NL/hr) | 343 | 333 |
| Desorbent flow rate (kg/hr) | 2.4 | 2.4 |
| Operating results | | |
| Ethylene purity (vol %) | 99.59% | 99.95% |
| Ethylene recovery rate (%) | 95.13% | 97.98% |

Table 8 above shows the performance of the ethylene displacement desorption process, obtained when the mixed gases having different compositions were used. As can be seen in Table 8 above, the process for recovering ethylene from composition II, that is, the gas containing 40% ethylene, was significantly advantageous in terms of ethylene purity and recovery rate. Thus, it could be seen that, when ethylene is recovered according to the present invention in which the pressure swing adsorption process and apparatus are used before recovering ethylene from the FCC off-gas, ethylene can be recovered in a higher yield.

As described above, the present invention provides the method and apparatus for recovering ethylene from an off-gas from fluidized catalytic cracking of heavy oils such as atmospheric residue, generated in a crude oil refining process. The method and apparatus of the present invention can reduce the amount of ethylene rinse in the subsequent ethylene displacement desorption process by increasing the ethylene purity of a raw material gas and reducing the concentration of weakly adsorbing components in the raw material gas and can reduce the loss of a desorbent during a distillation process for separating the desorbent from the weakly adsorbing components. Thus, according to the present invention, ethylene can be recovered from the off-gas from fluidized catalytic cracking of heavy oils at high concentration and low cost.

Although the preferred embodiments of the present invention have been described for illustrative purposes, those skilled in the art will appreciate that various modifications, additions and substitutions are possible, without departing from the scope and spirit of the invention as disclosed in the accompanying claims.

The invention claimed is:

1. A method for recovering ethylene from off-gas of a process for fluidized catalytic cracking (FCC) of a heavy oil fraction, the method comprising the processes of:
   concentrating C2+ components of the FCC off-gas using a pressure swing adsorption process to obtain a C2+ rich mixed gas; and introducing the C2+ rich mixed gas into a displacement desorption process to recover high-concentration ethylene from the mixed gas.

2. The method of claim 1, wherein the process of concentrating the C2+ components of the FCC off-gas using the pressure swing adsorption process comprises the steps of:
   i) introducing the FCC off-gas into an adsorption column packed with an adsorbent selectively adsorbing the C2+ components, so that the C2+ components are adsorbed onto the adsorbent and the remaining impurities are discharged out of the adsorption column;
   ii) discharging impurities from the adsorption column that was subjected to step i), by cocurrent depressurization;
   iii) countercurrently depressurizing the adsorption column that was subjected to step ii), while obtaining a partially concentrated C2 component;
   iv) recycling a portion of a gas discharged from the adsorption step into the adsorption column that was subjected to step iii), by low-pressure rinse, thereby desorbing C2+ components from the adsorption column;
   v) recycling a gas discharged from the adsorption step into the adsorption column that was subjected to step iv), and pressurizing the adsorption column; and
   vi) recycling a portion of a gas discharged from the adsorption step into the adsorption column that was subjected to step v), and pressurizing the adsorption column to the adsorption pressure.

3. The method of claim 1, wherein the process of concentrating the C2+ components of the FCC off-gas by the pressure swing adsorption process comprises the steps of:
   i) introducing the FCC off-gas into an adsorption column packed with an adsorbent selectively adsorbing the C2+ components, so that the C2+ components are adsorbed onto the adsorbent and the remaining impurities are discharged out of the adsorption column;
   ii) compressing a portion of a C2 rich stream obtained from countercurrent depressurization and low-pressure rinse and concurrently introducing the compressed stream into the adsorption column that was subjected to step i), thereby rinsing impurities away from the adsorption column with a C2 rich stream pressurized by a compressor so that the inside of the adsorption column becomes a C2+ rich atmosphere;
   iii) discharging impurities from the adsorption column that was subjected to step ii), by cocurrent depressurization;
   iv) countercurrently depressurizing the adsorption column that was subjected to step iii), while obtaining a partially concentrated C2 component;
   v) recycling a portion of a gas discharged from step i) into the adsorption column that was subjected to step iv), thereby desorbing C2+ components from the adsorption column by low-pressure rinse; and
   vi) recycling a gas discharged from step i) into the adsorption column that was subjected to step iv), and pressurizing the adsorption column to the adsorption pressure.

4. The method of claim 2, wherein each of steps i) to vi) is periodically repeated in at least two adsorption columns.

5. The method of claim 2, wherein the adsorbent selectively adsorbing the C2+ components is selected from the group consisting of silica gel, zeolite and activated carbon.

6. The method of claim 1, wherein the process of introducing the C2+ rich mixed gas into the displacement desorption process to recover high-concentration ethylene comprises:
   i) recovering gases resulting from adsorption and ethylene rinse into an adsorption column packed with an ethylene selective adsorbent;
   ii) introducing the C2+ rich mixed gas into the ethylene selective adsorbent-packed adsorption column to adsorb ethylene from the mixed gas, and introducing unadsorbed components and a desorbent, fed into the adsorption column during desorption, through the outlet of the adsorption column into a distillation column that separates an ethylene-poor stream/desorbent mixture into components;
   iii) introducing a high-concentration ethylene, obtained in a distillation column for separating an ethylene rich stream/desorbent mixture into components, into the adsorption column that was subjected to step ii), thereby removing ethane and other gases; and
   iv) introducing a desorbent into the adsorption column that was subjected to step iii) so as to desorb ethylene from the adsorption column, and then sending the desorbed ethylene into the distillation column for separating the ethylene rich stream/desorbent mixture into components, thereby producing concentrated ethylene.

7. The method of claim 1, wherein the process of introducing the C2+ rich mixed gas into the displacement desorption process to recover high-concentration ethylene comprises:
   i) introducing the C2+ rich mixed gas into the ethylene selective adsorbent-packed adsorption column to adsorb ethylene from the mixed gas, and introducing unadsorbed components and a desorbent, fed into the adsorption column during desorption, through the outlet of the adsorption column into a distillation column that separates an ethylene-poor stream/desorbent mixture into components;
   ii) recovering gases resulting from ethylene rinse into an adsorption column packed with an ethylene selective adsorbent;
   iii) introducing a high-concentration ethylene, obtained in a distillation column for separating an ethylene rich stream/desorbent mixture into components, into the adsorption column that was subjected to step ii), thereby removing ethane and other gases; and
   iv) introducing a desorbent into the adsorption column that was subjected to step iii) so as to desorb ethylene from the adsorption column, and then sending the desorbed ethylene into the distillation column for separating the ethylene rich stream/desorbent mixture into components, thereby producing concentrated ethylene.

8. The method of claim 6, wherein each of steps i) to iv) is periodically repeated in at least two adsorption columns.

9. The method of claim 6, wherein, if the pressure in step ii) is higher than atmospheric pressure, the method further comprises, before step iii), a step of discharging components other than ethylene by cocurrent depressurization.

10. The method of claim 6, wherein the method further comprises the steps of:
   v) communicating the adsorption column that was subjected to step i) with the adsorption column that was subjected to step iv) so as to send components other than ethylene from the adsorption column that was subjected to step i) to the adsorption column that was subjected to step (iv), thereby depressurizing the adsorption column that was subjected to step i) and pressurizing the adsorption column that was subjected to step v);
   vi) discharging components other than ethylene from the adsorption columns that was subjected to step v), by cocurrent depressurization; and
   vii) introducing the C2+ rich mixed gas into the adsorption columns that was subjected to step (vi), and pressurizing the adsorption columns to adsorption pressure.

11. The method of claim 6 or 7, wherein the ethylene selective adsorbent is a π-complex adsorbent selectively forming a π-complex with ethylene, a zeolite X adsorbent, a zeolite Y adsorbent, or a zeolite A adsorbent.

12. The method of claim 11, wherein the zeolite X adsorbent is a zeolite 13X adsorbent.

13. The method of claim 6, wherein the desorbent is a C3-C6 hydrocarbon.

14. The method of claim 6, wherein step iv) is carried out under conditions of a pressure of 1-10 atm and a temperature of 20-150° C.

15. The method of claim 6, wherein the desorbent obtained in the distillation column for separating the ethylene-poor stream/desorbent mixture into components and in the distillation column for separating the ethylene rich stream/desorbent mixture into components is recycled to the adsorption column.

16. The method of claim 3, wherein each of steps i) to vi) is periodically repeated in at least two adsorption columns.

17. The method of claim 3, wherein the adsorbent selectively adsorbing the C2+ components is selected from the group consisting of silica gel, zeolite and activated carbon.

18. The method of claim 7, wherein each of steps i) to iv is periodically repeated in at least two adsorption columns.

19. The method of claim 7, wherein, if the pressure in step ii) is higher than atmospheric pressure, the method further comprises, before step iii), a step of discharging components other than ethylene by cocurrent depressurization.

20. The method of claim 7, wherein the method further comprises the steps of:
   v) communicating the adsorption column that was subjected to step i) with the adsorption column that was subjected to step iv) so as to send components other than ethylene from the adsorption column that was subjected to step i) to the adsorption column that was subjected to step (iv), thereby depressurizing the adsorption column that was subjected to step i) and pressurizing the adsorption column that was subjected to step v);
   vi) discharging components other than ethylene from the adsorption columns that was subjected to step v), by cocurrent depressurization; and
   vii) introducing the C2+ rich mixed gas into the adsorption columns that was subjected to step (vi), and pressurizing the adsorption columns to adsorption pressure.

21. The method of claim 7, wherein the ethylene selective adsorbent is a π-complex adsorbent selectively forming a π-complex with ethylene, a zeolite X adsorbent, a zeolite Y adsorbent, or a zeolite A adsorbent.

22. The method of claim 21, wherein the zeolite X adsorbent is a zeolite 13X adsorbent.

23. The method of claim 7, wherein the desorbent is a C3-C6 hydrocarbon.

24. The method of claim 7, wherein step iv) is carried out under conditions of a pressure of 1-10 atm and a temperature of 20-150° C.

25. The method of claim 7, wherein the desorbent obtained in the distillation column for separating the ethylene-poor stream/desorbent mixture into components and in the distillation column for separating the ethylene rich stream/desorbent mixture into components is recycled to the adsorption column.

* * * * *